US010900945B2

(12) United States Patent
Hakimuddin (10) Patent No.: US 10,900,945 B2
(45) Date of Patent: Jan. 26, 2021

(54) TRI-AXIAL CENTRIFUGE APPARATUS WITH ELECTRICAL SENSOR, ACOUSTIC SENSOR, AND X-RAY INSTRUMENT

(71) Applicant: Saudi Arabian Oil Company, Dhahran (SA)

(72) Inventor: Mustafa Hakimuddin, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 582 days.

(21) Appl. No.: 14/514,747

(22) Filed: Oct. 15, 2014

(65) Prior Publication Data
US 2015/0111716 A1    Apr. 23, 2015

Related U.S. Application Data

(60) Provisional application No. 61/893,632, filed on Oct. 21, 2013.

(51) Int. Cl.
*G01N 33/24* (2006.01)
(52) U.S. Cl.
CPC .................................. *G01N 33/24* (2013.01)
(58) Field of Classification Search
CPC .................................. G01N 33/24; B04B 5/10
USPC ........................................................ 494/10, 37
See application file for complete search history.

(56) References Cited

U.S. PATENT DOCUMENTS

| 4,671,102 | A | | 6/1987 | Vinegar et al. |
| 5,159,828 | A | * | 11/1992 | Steiger ............. E21B 49/006 |
| | | | | 73/38 |
| 5,253,529 | A | | 10/1993 | Lenormand et al. |
| 5,265,461 | A | * | 11/1993 | Steiger ............... G01N 29/07 |
| | | | | 73/38 |
| 5,275,063 | A | | 1/1994 | Steiger et al. |
| 5,325,723 | A | | 7/1994 | Meadows et al. |
| 5,493,226 | A | | 2/1996 | Honarpour et al. |
| 5,568,262 | A | * | 10/1996 | LaChapelle ......... G01F 23/292 |
| | | | | 250/559.21 |
| 6,833,699 | B2 | | 12/2004 | Galford et al. |
| 6,971,260 | B2 | | 12/2005 | Potter |
| 7,055,374 | B2 | * | 6/2006 | Abdel-Hadi ............ G01N 3/08 |
| | | | | 73/38 |

(Continued)

FOREIGN PATENT DOCUMENTS

SU       1508147    *  9/1989
WO   WO 2004074762 A2 *  9/2004   ............... G01N 3/08

OTHER PUBLICATIONS

Josh et al., "Laboratory characterization of shale properties", Journal of Petroleum Science and Engineering, 2012, pp. 107-124, vol. 88-89, Elsevier.

(Continued)

*Primary Examiner* — Walter D. Griffin
*Assistant Examiner* — Shuyi S. Liu
(74) *Attorney, Agent, or Firm* — Bracewell LLP; Constance G. Rhebergen; Linda L. Morgan (57) ABSTRACT

The invention provides a tri-axial centrifuge apparatus for testing of petro-physical properties and gathering of geo-mechanical information, as well as methods of using the tri-axial centrifuge apparatus. The tri-axial centrifuge apparatus includes a tri-axial sample holder, a fluid sample holder, a centrifuge, at least one electrical sensor, at least one acoustic sensor, and an x-ray instrument.

12 Claims, 3 Drawing Sheets

(56) References Cited

U.S. PATENT DOCUMENTS

| | | | |
|---|---|---|---|
| 7,793,552 B2* | 9/2010 | Ng | G01N 33/24 73/760 |
| 8,024,960 B2 | 9/2011 | Fleury et al. | |
| 8,443,661 B1* | 5/2013 | Bi | G01N 33/24 73/152.05 |
| 2005/0103094 A1* | 5/2005 | Knight | G01N 15/0826 73/38 |
| 2005/0150273 A1 | 7/2005 | Potter | |
| 2005/0183859 A1 | 8/2005 | Seams | |
| 2006/0070425 A1* | 4/2006 | Lasswell | G01N 15/0886 73/38 |
| 2010/0274367 A1* | 10/2010 | Kaufman | G06F 17/5009 700/31 |
| 2010/0313645 A1 | 12/2010 | Doman et al. | |
| 2011/0050223 A1 | 3/2011 | Balcom et al. | |
| 2012/0118041 A1 | 5/2012 | He et al. | |
| 2012/0151998 A1 | 6/2012 | Willberg et al. | |
| 2012/0304763 A1* | 12/2012 | Troxler | G01B 11/00 73/32 R |
| 2013/0228019 A1 | 9/2013 | Meadows et al. | |

OTHER PUBLICATIONS

Kenyon et al., "NMR in partially saturated rocks: Laboratory insights on free fluid index and comparison with borehole logs", SPWLA, 1991, 1pgs, Society of Petrophysicists & Well Log Analysts (Abstract).

Kuila et al., "Stress anisotropy and velocity anisotropy in low porosity shale", Tectonophysics, 2011, pp. 34-44, vol. 53, Elsevier.

Meissner et al., "State of the Art Special Core Analysis Program Design and Results for Effective Reservoir Management", International Petroleum Technology Conference, Doha, Qatar, 2009, 1pgs, (Abstract).

O'Meara Jr. et al., "Centrifuge Measurements of Capillary Pressure: Part 1—Outflow Boundary Condition", SPE, 1992, 1 pgs, Society of Petroleum Engineers (Abstract).

Onitsuka et al., "A study on the relationship between mechanical properties and microstructure of Ariake Clay", ISOPE, 1999, 1pgs, The International Society of Offshore and Polar Engineers (Abstract).

Sarout et al., "Shale dynamic properties and anisotropy under triaxial loading: Experimental and theoretical investigations", Physics and Chemistry of the Earth, 2007, pp. 896-906, vol. 32, Elsevier.

Unalmiser et al., "Engineering Core Analysis", Distinguished Author Series, 1998, pp. 106-112, SPE 36780.

Yao et al., Petrophysical characterization of coals by low-field nuclear magnetic resonance (NMR), Fuel, 2010, pp. 1371-1380, vol. 89, Elsevier.

PCT International Search Report and the Written Opinion; dated Feb. 25, 2015; International Application No. PCT/US2014/061313; International File Date: Oct. 20, 2014.

Chryssanthakis et al., "High temperature triaxial tests with ultrasonic measurement on Ekofisk chalk", Rock Mechanics for Industry, 1999, pp. 373-379, www.onepetro.org/conference-paper/ARMA-99-0373.

Wang et al., "Simultaneous core sample measurements of elastic properties and resistivity at reservoir conditions employing a modified triaxial cell—a feasibility study", Geophysical Prospecting, 2009, pp. 1009-1026, vol. 57, EAGE.

Sze, et al.,"Physical Experimentation Research of Rock in Medium-Deep Natural Gas Reservoir", Chinese Masters Thesis Full-Text Database Basic Sciences; pp. A011-41, Mar. 15, 2008, vol. 3.

* cited by examiner

TRI-AXIAL CENTRIFUGE APPARATUS WITH ELECTRICAL SENSOR, ACOUSTIC SENSOR, AND X-RAY INSTRUMENT

This application claims priority to U.S. Provisional Application No. 61/893,632, filed on Oct. 21, 2013, titled "Tri-Axial Centrifuge Apparatus."

FIELD OF THE INVENTION

Generally, this invention relates to a tri-axial centrifuge apparatus for testing of petro-physical properties and gathering of geo-mechanical information.

BACKGROUND OF THE INVENTION

There are a number of limitations related to methods, techniques, and instruments utilized for reservoir sample testing and analysis. The most basic step in any reservoir study is sample preparation. Improper or ineffective cleaning practice to bring a sample to a native (original) state can render all efforts of testing and analyses in vain. This step is the most detrimental to sample analysis, especially in tight unconventional formations, gas shales, and conventional formations of dual porosities. The various current cleaning process have limitations of achieving proper capillary pressure to effectively remove impurities from test samples in order to prepare them for tests and analysis. Attempts to overcome these issues by utilizing harsh processes of heated solvents or high flow methods are ineffective. In many instances, such practices alter the wettability of test sample, thus defeating the primary purpose of cleaning the test sample. These artificial alterations in wettability and fluid saturations caused by various known sample restoration techniques create significant errors in petro-physical data collected for reservoir evaluation. In unconventional (gas shale) reservoir analysis, the conventional cleaning procedures are also largely ineffective because they do not take into account the capillary effect. When the reservoir is formed, hydrocarbons migrate into reservoir rock replacing water that was initially present. This is a capillary driven mechanism and there is a need to recreate this scenario in laboratory studies to mimic the reservoir process.

Once a sample is restored, it can then be subjected to various petro-physical tests and analyses. Currently, there are a series of tests performed on different instruments to obtain various petro-physical data needed for reservoir characterization and production analysis. Typically, several instruments are used to perform electrical properties analysis to calibrate the electrical log, fluid saturation analysis, and analysis of Archie's parameters. Another apparatus is needed to perform capillary pressure above 1000 psi analysis, one to perform fluid wettability analysis, one to perform acoustic velocity for dynamic mechanical properties, and yet another apparatus to perform x-ray for saturation distribution. Currently, there is no instrument that can perform many of these tests under tri-axial conditions that are observed in the field.

The need of such an apparatus is immense, especially for evaluation of unconventional sources, such as tight gas sand, shale, tar sand, and hydrates, as the conventional apparatus in the industry do not perform adequate analysis of these formations.

Additionally, existing centrifuge methods are flawed. The sample holders used in existing centrifuges cannot apply tri-axial stress on the sample, as such samples typically fail at RPM higher than 10,000. The capillary pressure such centrifuge devices can attain is not sufficiently high enough to duplicate conditions found in some reservoirs, especially unconventional and depleted reservoirs. With many of the current centrifuge methods, the measurement for saturation is based on fluid differentiation and does not incorporate the actual distribution of fluid in a test sample. Additionally, the test chambers typically used to hold the test sample cannot handle most of the corrosive chemicals that are required during the life cycle of sample tests (e.g., solvents, inhibitors, surfactant, enhanced oil recovery (EOR) chemicals and acids). Another concern with current centrifuge methods is that the necessary measurements of rock electrical properties are not collected continuously throughout the test. Additionally, the orientation of the test specimen and its distance from the center of the centrifuge axis, has been problematic with current centrifuge methods.

In every stage of reservoir exploitation, accurate information about fluid saturation, pore distribution, capillary pressure, and permeability is vital. In the exploration stage, such information provides estimates for original hydrocarbon in-place and maximum primary production. In later stages of reservoir life cycle, it helps determine various secondary and tertiary enhanced oil recovery options, particularly for a most cost effective and profitable scenario. During abandonment of the well, the saturation values are imperative to assist in the design of a proper abandonment, such as complete shut off or maintenance for possible future intervention.

SUMMARY

In one aspect, the invention provides a tri-axial centrifuge apparatus for testing of petro-physical properties and gathering of geo-mechanical information. The tri-axial centrifuge apparatus includes a tri-axial sample holder, a fluid sample holder, a centrifuge, at least one electrical sensor, at least one acoustic sensor, and an x-ray instrument.

In another aspect, the invention provides a method of using the tri-axial centrifuge apparatus. The method includes obtaining a test sample from a reservoir. The test sample is then loaded in the tri-axial sample holder. The tri-axial sample holder is loaded in the tri-axial test casing. An axial pressure is applied to the tri-axial test casing. The confining pressure is increased to the tri-axial test casing. The pressure, fluid, and temperature are equilibrated for the test sample. The fluid sample holder is loaded in the tri-axial test casing. A centrifuge test is performed on the test sample. An x-ray scan of the test sample is performed. Electrical analysis of the test sample is performed. Acoustic analysis of the test sample is also performed.

DETAILED DESCRIPTION OF THE INVENTION

Although the following detailed description contains many specific details for purposes of illustration, it is understood that one of ordinary skill in the art will appreciate that many examples, variations, and alterations to the following details are within the scope and spirit of the invention. Accordingly, the exemplary embodiments of the invention described herein and provided in the appended figures are set forth without any loss of generality, and without imposing limitations, on the claimed invention.

Figure 1:
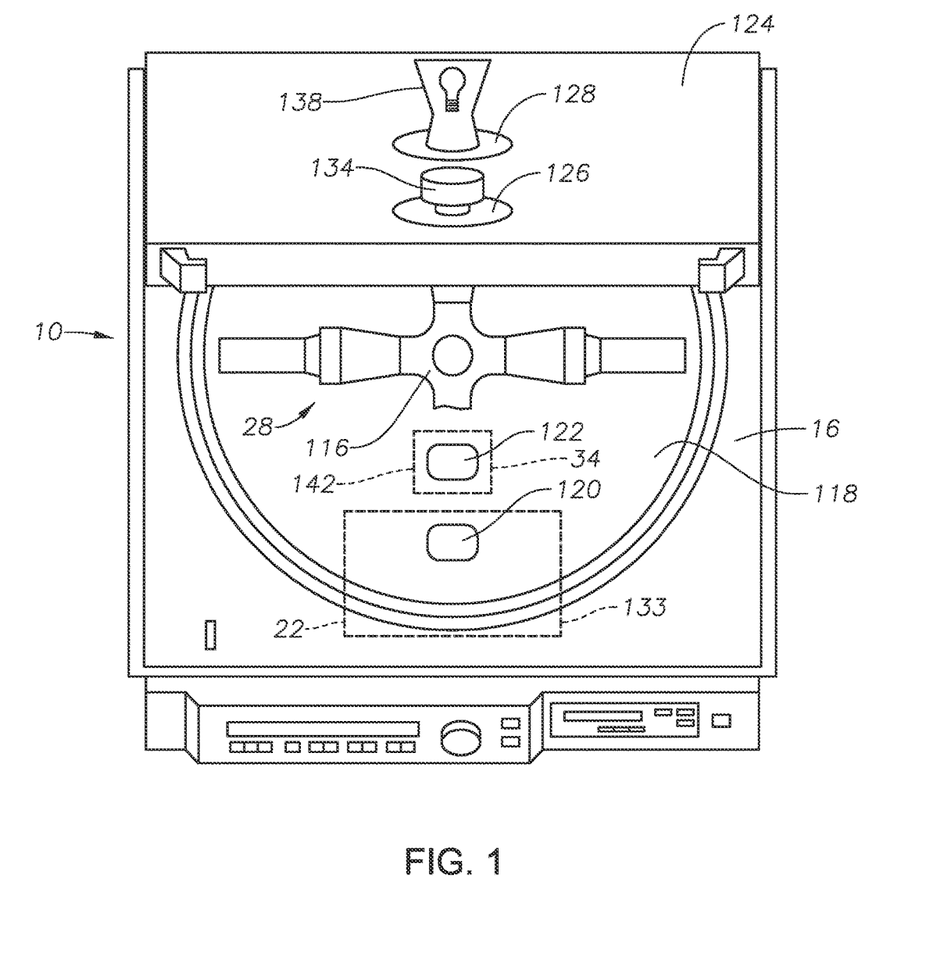
FIG. 1 is a schematic perspective view of a tri-axial centrifuge apparatus with the centrifuge lid open, according to an embodiment of this disclosure.
Figure 2:
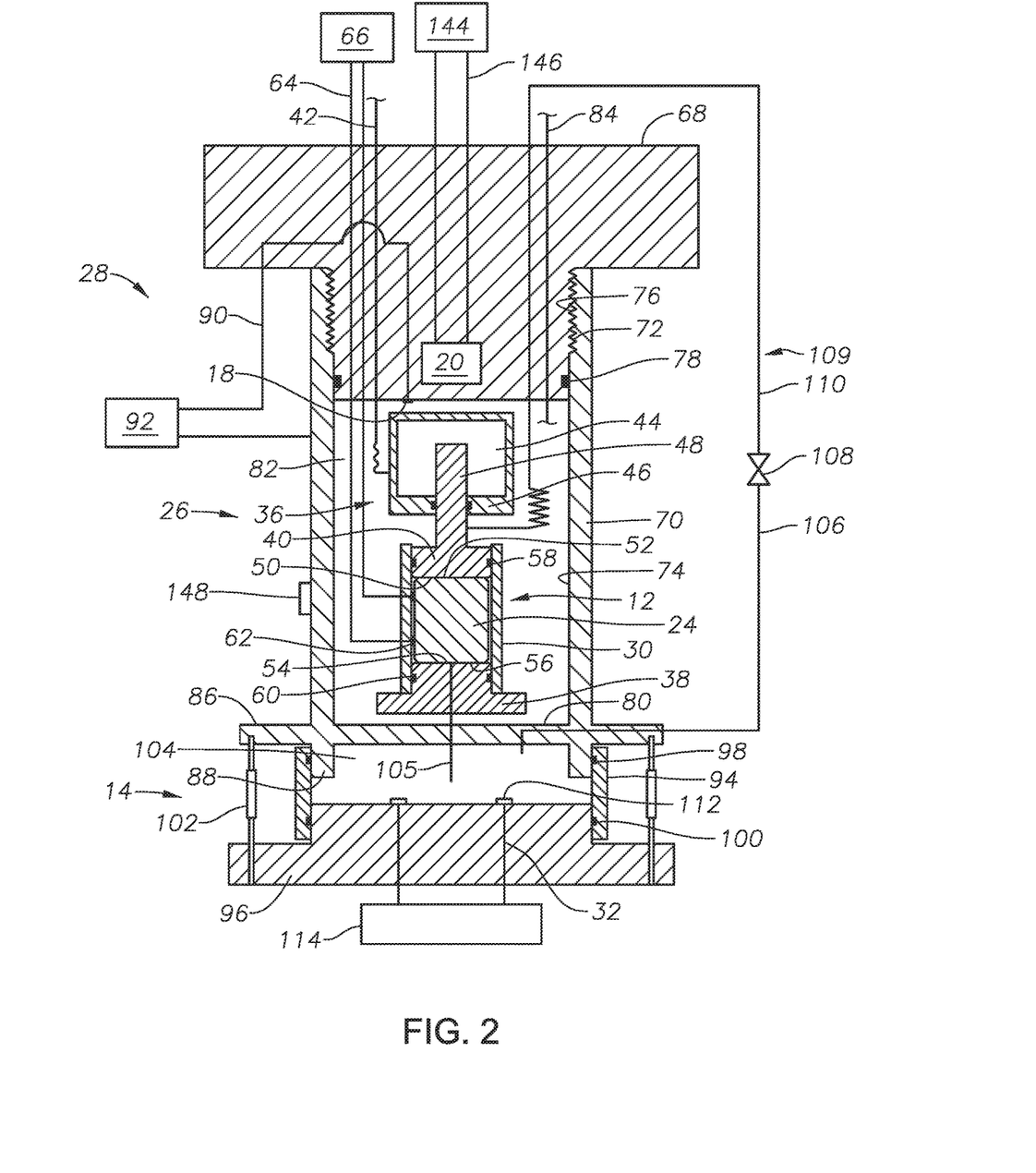
FIG. 2 is a schematic sectional view of a tri-axial cell assembly of the tri-axial centrifuge apparatus of FIG. 1.

Looking at FIGS. 1 and 2, the invention provides a tri-axial centrifuge apparatus 10 for testing of petro-physical properties and gathering of geo-mechanical information. The tri-axial centrifuge apparatus 10 includes a tri-axial sample holder 12 and a fluid sample holder 14. The tri-axial centrifuge apparatus 10 also includes a centrifuge 16, at least one electrical sensor 18, at least one acoustic sensor 20, and an x-ray instrument 22.

In another aspect, the invention provides a method of using the tri-axial centrifuge apparatus 10. The method includes obtaining a test sample 24 from a reservoir. In some embodiments, the test sample 24 will be a reservoir rock with some reservoir fluid within it under ambient conditions of temperature and pressure. In some embodiments, such as a lab setting, the test sample 24 can be a frozen rock sample with much more reservoir fluids in the rock sample, but still under ambient pressure and lower temperature. The test sample 24 is then loaded in the tri-axial sample holder 12. The tri-axial sample holder 12 is loaded in a tri-axial test casing 26. A tri-axial pressure is applied to the tri-axial test casing 26 and the confining pressure is increased in the tri-axial test casing 26. The pressure, temperature, and fluids are equilibrated for the test sample 24. The fluid sample holder 14 is installed on the tri-axial test casing 26. A centrifuge test is performed on the test sample 24. An x-ray scan of the test sample 24 is performed. Electrical analysis of the test sample 24 is performed. Acoustic analysis of the test sample 24 is also performed.

Embodiments of the present invention allow a tri-axial load to be applied to a test sample 24 to simulate the in-situ conditions of a reservoir. Additionally, the high RPM of the centrifuge 16 provides the capillary pressure similar to that experienced in-situ. In general, the RPM is selected based on how much capillary pressure is required to achieve appropriate test conditions for a selected sample. For conventional reservoir rock, a capillary pressure of 500 psi (equivalent to about 12,000 RPM) can be sufficient, but for an unconventional reservoir sample, a capillary pressure of 1500 psi or higher can be required (equivalent to about 27,000 RPM or higher). Further embodiments of the invention provide a solvent resistant assembly which allows for usage of solvents for stripping hydrocarbons, water, and salt from the samples. The use of titanium, Teflon®, Torlon®, and/or glass instead of conventionally used materials allows for a solvent resistant assembly. The typical solvent mix used in experiments can include toluene, methanol, xylene, chloroform, water, acids, and other industrial hydrocarbon based solvents.

In some embodiments, the tri-axial centrifuge apparatus 10 is capable of performing one or more of the centrifuge test, x-ray scan, electrical analysis, and acoustic analysis simultaneously, thus allowing an efficient and comprehensive test sample study to be performed. An added advantage of such testing is that the continuous stressing, distressing, and handling of a test sample 24 for performing each of the test separately in different instruments, is removed. Additionally, embodiments of the present invention allow for integration of the various data collected related to various sample properties and allow for better reservoir modeling. For example, data collected from acoustic (sonic) monitoring during capillary pressure measurements will provide information about the mechanical stress changes on the test sample 24, not only as a function of pressure change but also as the formation fluid changes. This information can be used during seismic monitoring of reservoir production and for tuning simulation for production profiles. In further embodiments, the various tests and analyses are performed in sequential steps.

Still looking at FIGS. 1 and 2, the base design of the tri-axial centrifuge apparatus 10 includes a tri-axial sample holder 12, a fluid sample holder 14, a centrifuge 16, at least one electrical sensor 18, at least one acoustic sensor 20, and an x-ray instrument 22. In other embodiments, the tri-axial centrifuge apparatus 10 includes a tri-axial cell assembly 28. The tri-axial cell assembly 28 includes a tri-axial test casing 26, a tri-axial sample holder 12 and a fluid sample holder 14. Further embodiments also include at least one of the following: an electrical measurement jacket 30, electrical measurement feeds 32 associated with the fluid sample holder 14, and a fluid camera system 34.

Tri-Axial Sample Holder: Turning to FIG. 1, the tri-axial sample holder 12 is configured to hold the solid test samples 24 from a reservoir. The tri-axial sample holder 12 includes a piston assembly 36 and a base member 38. In general, materials for the piston assembly 36 and base member 38 should be penetrable to x-rays and have minimal or no electrical conductance and can be, for example, Torlon® (available from Solvay Plastics) or glass. Piston assembly 36 includes a piston member 40, and a fluid chamber 44. An axial pressure fluid supply line 42 supplies fluid to fluid chamber 44. A fluid chamber base 46 has an opening through which the stem 48 of piston member 40 extends. An end face 50 of piston member 40 engages a first end 52 of test sample 24.

Base member 38 has an end face 54 that engages a second end 56 of test sample 24 that is opposite the first end 52 of test sample 24. Test sample 24 is therefore contained between the end face 50 of piston member 40 and the end face 54 of base member 38. As fluid is added to the fluid chamber 44 by way of axial pressure fluid supply line 42, the end face 50 of piston member 40 will apply axial force on the first end 52 of test sample 24, inducing axial stress in test sample 24. End face 50 of piston assembly 36 and end face 54 of base member 38 can be coated with a substance, such as Teflon®, that will provide electrical isolation of the test sample 24.

Electrical Measurement Jacket: In certain embodiments, the tri-axial sample holder includes the electrical measurement jacket 30. The electrical measurement jacket 30 is a non-permeable, elastomeric, rubber or polyurethane jacket and can be made, for example, of Viton® (available from DuPont). Electrical measurement jacket 30 is a tubular member that surrounds the test sample 24. A piston seal 58 forms a seal between the inner bore of a first end of electrical measurement jacket 30 and an outer surface of piston member 40. A base seal 60 forms a seal between the inner bore of a second end of the electrical measurement jacket 30 and an outer surface of base member 38.

The electrical measurement jacket 30 is equipped with jacket sensors 62 to provide additional measurements of electrical properties of the test sample and saturation distribution data. The electrical measurement jacket 30 is made by incorporating the conductive jacket sensors 62 during a vulcanization process of jacket making The type of jacket sensors 62, number of sensors, and their location is based on sample size and sample property, such as its mineral composition and homogeneity. The number of jacket sensors 62 in the electrical measurement jacket 30 can be increased and distributed such that various electrical measurements are performed on the test sample 24 and the collected electrical measurement values can provide an electrical image. The data collected by the jacket sensors 62 can be transmitted by way of leads 64 to a processing unit 66. This type of data gathering can be extremely valuable for heterogeneous samples with layering, unconnected pore structure, fracture, kerogen concentration, and other sample anomalies. The data from multiple conductive jacket sensors 62 can be used measure electrical resistance across the test sample 24 and to produce an image of rock lithology and geology.

Tri-Axial Test Casing: Continuing to look at FIG. 1, the tri-axial sample holder 12 is located within the tri-axial test casing 26. Tri-axial test casing 26 includes a top end cap 68 and a cell body 70. Top end cap 68 has external threads 72 located on an outer surface of a reduced diameter portion of top end cap 68. Cell body 70 is a generally cylindrical member with an inner bore 74. Cell body 70 has internal threads 76 that extend from a cap end of the cell body 70 on an inner surface of inner bore 74 that mate with external threads 72 of top end cap 68. A circumferential casing seal 78 creates a seal between the inner surface of inner bore 74 and the outer surface of the reduced diameter portion of top end cap 68.

Cell body 70 has a bulkhead 80 proximate to a base end of cell body 70 that is opposite the cap end. Bulkhead 80 is a plate that extends fully across inner bore 74, so that a cell chamber 82 is defined by bulkhead 80, the inner surface of inner bore 74, and top end cap 68. A confining pressure fluid supply line 84 delivers fluid to cell chamber 82 for applying biaxial stress on the test sample 24. Bulkhead 80 has an enlarged diameter extending outward to define a circumferential flange 86. Bulkhead 80 is located a distance from the base end of cell body 70 defining a skirt 88 formed by a portion of cell body 70 and inner bore 74 that extend past bulkhead 80.

In some embodiments, the tri-axial test casing 26 is made of titanium. Titanium allows for x-ray scanning while the test is in progress. In other embodiments, the tri-axial test casing 26 is made of Torlon® or glass. In general, materials for the tri-axial cell assembly 28 should be penetrable to x-rays and have minimal or no electrical conductance. In further embodiments, the tri-axial test casing 26 and tri-axial sample holder 12 include both internal and external coatings that are resistant to acids and corrosive chemicals, such as hydrochloric acid, acetic acid, or other acids that would be used to mimic well cleaning and stimulation tests, as well as acids that would be used for chemical EOR. The tri-axial cell assembly 28 is capable of performing centrifuge saturation and capillary pressure test at unconfined, hydrostatic, or tri-axial test conditions.

The tri-axial sample holder 12 is equipped with an acoustic sensor 20 with p-wave and s-wave components. Acoustic sensor 20 can be a dual mode transducer capable of both sending and receiving information. In some embodiments, the acoustic sensor 20 is located on or in the top end cap 68. In some embodiments, the top end cap 68 is isolated from the cell body 70 of the tri-axial sample holder 12 such that electrical properties can be measured using electrical sensors 18 in the top end cap 68 and the cell body 70 of the tri-axial sample holder 12 as ground. In such an embodiment, electrical sensors 18 of top end cap 68 can provide electrical information by way of leads 90 to a processing unit 92.

Fluid Sample Holder: Continuing to refer to FIG. 2, the tri-axial cell assembly 28 includes a tri-axial test casing 26, a tri-axial sample holder 12 and a fluid sample holder 14.

The fluid sample holder 14 is configured to hold the fluid samples. Depending on the test type, the fluid sample holder 14 can hold fluid samples from the test sample 24, or fluids to be injected into the test sample 24 such as solvents, acids, or chemicals for EOR.

Fluid sample holder 14 includes a fluid sample ring 94 and a fluid sample base 96. In some embodiments, the fluid sample ring 94 is made of glass. In further embodiments, the fluid sample ring 94 is made of temperature treated, industrial grade glass, such as Pyrex® glass. Fluid sample rings 94 of various thicknesses can be used to accommodate various volumes of fluids. In general, glass, especially temperature treated, industrial grade glass, is preferred because it provides clear readings for capturing various fluid volumes produced. Additionally, glass is neutral with respect to wettability, and it separates air, water, and hydrocarbon fluids quickly. Glass also can be used with almost all known chemical and corrosive fluids, without negative reaction.

Fluid sample base 96 is a generally cylindrical member and can be formed of metallic or non-metallic materials. Fluid sample ring 94 extends from skirt 88 of cell body 70 to a reduced diameter portion of fluid sample base 96. A first fluid sample seal 98 creates a seal between an inner surface of the fluid sample ring 94 and an outer surface of skirt 88. A second fluid sample seal 100 creates a seal between an inner surface of the fluid sample ring 94 and an outer surface of the reduced diameter portion of fluid sample base 96. Double ended screws 102 releasably join circumferential flange 86 of cell body 70 to an enlarged diameter portion of fluid sample base 96. By joining fluid sample base 96 to cell body 70, fluid sample ring 94 is maintained in position relative to tri-axial test casing 26.

A fluid reservoir 104 is defined by the inner bore of fluid sample ring 94, a face of bulkhead 80 and a surface of fluid sample base 96. A test sample fluid line 105 carries fluid from the tri-axial sample holder 12 to the fluid reservoir 104. A first fluid circulation line 106 carries fluid between the fluid reservoir 104 and an isolation valve 108. A second fluid circulation line 110 carries fluid between the isolation valve 108 and the tri-axial sample holder 12. Test sample fluid line 105 first fluid circulation line 106 and second fluid circulation line 110 together form test fluid circulation system 109. Isolation valve 108 can be used during the setup of the test to manage the fluids and can provide a connection point between the first and second fluid circulation lines 106, 110.

In further embodiments, the tri-axial centrifuge apparatus 10 includes electrical measurement feeds 32 associated with the fluid sample holder 14. The fluid sample holder 14 is designed such that the fluid sample base 96 is made of material that is electrically insulated and is embedded with electrodes 12 for performing 2 or 4 electrode conductivity and resistivity measurements. The electrical measurement feeds 32 are connected to electrodes 112 of the fluid sample holder 14 to deliver signals to a processing unit 114 for data collection regarding reservoir salinity information from native state samples which will allow for better reserve estimation. In certain embodiments, the electrical measurement feeds 32 can provide current and measure the voltage with a small battery operated device (not shown) that can be installed on the rotor 116 of centrifuge 16 (FIG. 1) and connected to the tri-axial cell assembly 28.

Figure 3:
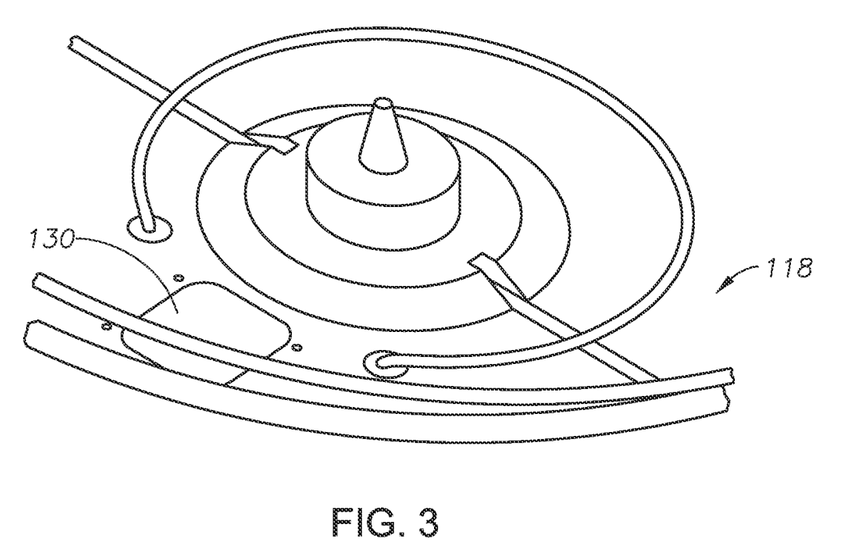
FIG. 3 is a sectional view of a bottom portion of a tri-axial centrifuge apparatus according to an embodiment of this disclosure.
Figure 4:
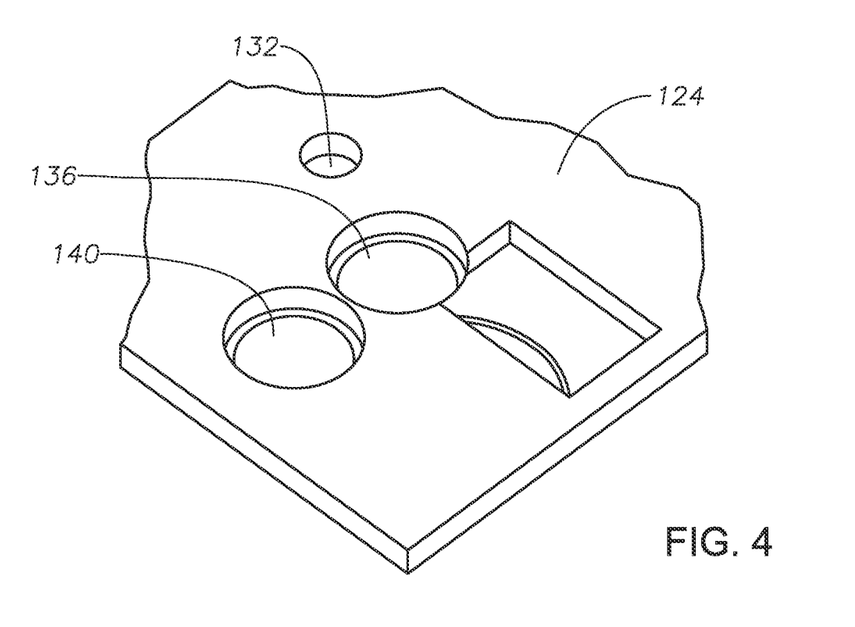
FIG. 4 is a sectional view of a lid portion of the tri-axial centrifuge apparatus according to an embodiment of this disclosure.

Centrifuge: Returning to FIG. 1, any centrifuge 16 that can work within the provided test parameters will be acceptable for use in this invention. In some embodiments, a centrifuge such as the Hettich centrifuge Roto-Salina, which is outfitted for a higher RPM (20,000 rpm and higher) is preferred. Such centrifuges have tubs 118 with larger diameters which provide a higher capillary pressure at a given RPM as compared to industry standard centrifuges. In the embodiment of FIG. 1, the rotor 116 of the centrifuge 16 is shown with 4 tri-axial cell assemblies 28. In some embodiments, the rotor 116 of the centrifuge 16 is designed to hold 1, 2, 3, or 6 tri-axial cell assemblies 28. The number of tri-axial cell assemblies 28 that can be placed in the rotor 116 will be based on specific test parameters. Centrifuge 16 has a window that is located on a portion of a path of the tri-axis sample holder 12. In some embodiments, the bowl or tub 118 of the centrifuge 16 has at least two glass tub windows 120, 122 for x-ray scanning and the fluid camera system 34, respectively. In further embodiments, the top or lid 124 of the centrifuge 16 has two lid windows 126, 128 aligned with the tub windows 120, 122 for x-ray scanning and the fluid camera system 34, respectively. In further embodiments, the tub 118 and the lid 124 each have a single window that can be used for both x-ray scanning and the fluid camera system 34. In yet further embodiments, as shown in FIGS. 3-4, the tub 118 has a single tub window 130 for x-ray source 133 (FIG. 1) and the lid 124 has a first lid window 132 opposite the single tub window 130 for x-ray camera 134 (FIG. 1). In such an embodiment, lid 124 has a second lid window 136 for a visual camera light source 138 (FIG. 1) and a third lid window 140 for visual camera 142 (FIG. 1).

Electrical sensors: Returning to FIG. 1, a variety of electrical measurements can be taken during testing. For instance, in some embodiments electrical analysis of the test sample 24 includes measuring at least one of the resistance, conductivity, capacitance, or impedance of the test sample. In some embodiments, electrical analysis of the test sample 24 includes measuring at least one of electrical conductance, resistance, or impedance as a function of variable frequency of input current. In some embodiments, the top end cap 68 of the tri-axial test casing 26 is designed such that it is isolated from the rest of the tri-axial test casing 26 and acts as an electrode. The cell body 70 of the tri-axial test casing 26 can be used as a ground to measure the electrical properties of the test sample 24 during a test. Electrical measurements can be taken at least one of two ways during a test. In the first, the centrifuge 16 is stopped at each capillary pressure equilibrium step, taking the tri-axial test casing 26 out, and measuring the electrical properties. Depending on the test design, additional equilibrium steps can be required. In some embodiments, there can be 2 to 15 equilibrium steps and measurements can be performed at each step. In a second method, processing unit 92 is a battery operated electrical measurement device with capability to gather the time domain data that can be down loaded at the end of test. The advantage of the second method is that it provides a continuous measurement without a need of stopping centrifuge 16 and also provides transit data between the capillary pressure equilibrium stages. Thus, a preferred embodiment of the present invention includes an processing unit 92 that is operable to gather data during the testing of a sample and store data for downloading at a later time. In further embodiments, the data is downloaded in real time. In further embodiments, the electrical data collected on the test sample 24 can be collected simultaneously as the other data is collected, or in sequential steps to the other data. In further embodiments, an electrical sensor 18 measures the electrical properties of fluid contacting the surface of the tri-axial test casing 26.

Acoustic sensors: A variety of acoustic measurements can be taken during testing, including sonic velocity data. In some embodiments, the acoustic sensor 20 can collect longitudinal wave, shear wave, and/or Stonely wave data. The acoustic data collected can be delivered to processing unit 144 by way of leads 146 and analyzed for both time and frequency domain. The same acoustic sensor 20 can collect the various wave forms, as one transducer can encompass crystals for longitudinal and shear wave. In preferred embodiments, the acoustic sensor 20 is a transducer with both longitudinal wave and shear wave components which are installed on the top end cap 68 of the tri-axial test casing 26. In some embodiments, the acoustic sensor 20 is a dual mode transducer and works in reflective mode to transmit and receive acoustic wave. In some embodiments, the tri-axial centrifuge apparatus 10 is operable to measure the acoustic velocity of the test sample 24, as well as the velocities of the various fluids in the fluid sample holder 14. The same acoustic sensor 20 can perform all of the desired the measurements with proper calibration of the acoustic sensor 20 before the test starts and once the test is concluded, dependent on rock sample properties and fluid used during the test. The acoustic velocity of the fluid in the fluid sample holder 14 can be used to analyze production and presence of solid particles such as grain, asphaltene, and so forth. In general, special care should be taken to assure that the acoustic sensor 20 and associated components does not interfere with electrical measurements. The acoustic data collected on the test sample 24 can be collected simultaneously with the other data, or in sequential steps to the other data.

X-Ray: X-ray instrument 22 can be any x-ray that allows for scanning of a moving object. For example, Hamamatsu manufactures such devices. The x-ray instrument 22 shown in FIG. 1 includes an x-ray source 133 and an x-ray camera 134. In the embodiment of FIGS. 1 and 3-4, the x-ray source 133 is located below the centrifuge tub 118 while the x-ray camera (image capture system) 134 is installed on the lid 124 of the centrifuge 16. The x-ray instrument 22 is static and is aligned with a window of the centrifuge 16. The x-ray instrument 22 is capable of performing a whole sample scan which provides accurate saturation profiles of various fluids in the test sample 24 at each equilibrium stage while the centrifuge 16 is spinning However, there is a RPM limitation on the x-ray instrument 22, so a different technique is utilized at higher RPM. For instance, at higher RPM, such as about 10,000 and above, once the equilibrium for fluids is achieved, the RPM can be reduced to a lower RPM, such as 2,000 RPM for sample scanning, and then the RPM can be raised back to the original higher RPM of about 10,000 and above. This does not affect the saturation distribution as equilibrium is already achieved before lowering the RPM. In certain embodiments, the x-ray instrument 22 can allow for computed tomography (CT) imaging.

Fluid Camera System: Looking at FIG. 1, in further embodiments, the tri-axial centrifuge apparatus 10 includes a visual fluid camera system. The fluid camera system 34 includes visual camera light source 138 and a visual camera 142. Visual camera light source 138 can be a strobe light source and visual camera 142 can be a high speed camera to capture images as the test progress. The image capturing and fluid level analysis is greatly aided by use of glass throughout the tri-axial centrifuge apparatus 10, which provides for clear images and sharp contrast between various fluids. The fluid camera system 34 is designed to work both in transmission and reflection mode, i.e., the visual camera light source 138 and visual camera 142 can be installed on the opposite side of the test sample 24 (e.g., top and bottom) or on the same side (e.g., top) and use a reflective mirror setup in the tub 118 to capture images. The mirror setup can be utilized in cases of limited access on the tub. In the embodiment of FIG. 1, the visual camera light source 138 is installed above the lid 124 of the centrifuge 16 and visual camera 142 is installed below the centrifuge tub 118. In the embodiment of FIGS. 3-4, both the visual camera light source 138 and visual camera 142 are installed above the lid 124 of centrifuge 16. Use of such a fluid camera system 34 allows for reading of fluid volumes as they are produced.

Temperature Sensor: The temperature sensors 148 used in embodiments of the invention include typical infrared high precision temperature probes that are available off the shelf. For example, such temperature sensors are available from Raytek. Temperature sensors 148 can be positioned in multiple locations on or around tri-axial centrifuge apparatus 10.

Centrifuge capillary pressure under tri-axial, confining, and unconfined stress conditions can be performed with the tri-axial centrifuge apparatus 10. In some embodiments, capillary pressure over 20,000 psi for an oil/gas/water system can be analyzed. The range of capillary pressures to be tested will depends on the type of reservoir. For example, for unconsolidated sand reservoirs, capillary pressures can range from 0.1 psi to 100 psi; for conventional reservoirs capillary pressures can range from 1 psi to 200 psi; for unconventional reservoirs like shale and tight gas sand (TGS), capillary pressures can range from 100-100,000 psi. It should be noted that in instances with a capillary pressure of above 30,000 psi, sample integrity can be an issue. In many such cases, a work around can be developed by increasing the tri-axial stress. The test can be conducted as air/water, air/oil, water/oil and in limited cases all three phases (air/oil/water) on the rock sample. Thus, embodiments of the present invention allow for extracting of reservoir core samples with hydrocarbon solvents at capillary pressure of 20,000 psi and higher. In some embodiments, capillary pressure above 20,000 psi is achieved by expanding motor speed (RPM), increasing the size of tub 118, increasing the distance between the test sample 24 and center of centrifuge 16, and changing sample size and orientation. In some embodiments, the test sample 24 is loaded in the centrifuge 16 in a vertical orientation. In other embodiments, the test sample 24 is loaded in the centrifuge 16 in a horizontal orientation. In some embodiments, the test sample 24 can be about 0.5 inches to about 8 inches in diameter and about 0.5 inches to about 12 inches in length or smaller.

The large range of data collected (acoustic, temperature, electrical, x-ray, saturation, fluid volumes, rate of fluid volumes, and saturation change) provides a more complete picture of test progression that can be integrated with log and seismic data for monitoring and evaluating effectiveness of field treatment. Temperature can be monitored using the temperature sensors 148, rate of fluid volumes can be monitored using the fluid camera system 34, and saturation changes can be monitored with the x-ray instrument 22. For example, electrical data can be generated for the wells where logs are not available or are not representative with a combination of seismic, acoustic, electrical and saturation data, along with well test information.

Test sample preparation: In some embodiments, the invention provides the ability to use solvents to establish the test sample's 24 saturation and to bring test sample 24 to a virgin clean state. Given that the tri-axial centrifuge apparatus 10 and its components are made of solvent resistant material, the tri-axial centrifuge apparatus 10 allows for sample cleaning within centrifuge 16 setup. The procedure will vary based on solvents to be used. A given test sample 24 can be cleaned with multiple solvents. In some embodiments, for each solvent, the tri-axial cell assembly 28 will be removed from centrifuge 16 and the fluid sample holder 14 will be filled with the desired solvent. The test sample 24 will then be centrifuged with that solvent. This step can be repeated until all desired solvents have been used. In further embodiments, each cleaning step can involve the use of more than one solvent.

An exemplary test procedure according to an embodiment of the invention is provided according to the following steps. A test sample 24 is obtained from a reservoir. The tri-axial centrifuge apparatus 10 and test sample 24 are prepared based on test sample 24 condition and test requirements. The test sample 24 is loaded in the tri-axial sample holder 12 and placed in an electrical measurement jacket 30. The assembled jacketed tri-axial sample holder 12 is loaded in the cell body 70 of tri-axial test casing 26 and the top end cap 68 is screwed on, making sure the test sample fluid line 105 from the jacketed tri-axial sample holder 12 is extending out of the bulkhead 80 of the tri-axial test casing 26. As the top end cap 68 is tightened, the rotation of the test sample fluid line 105 is monitored for twisting. As the top end cap 68 is tightened, the test sample fluid line 105 should not twist. The axial stress on the test sample 24 is slowly increased by injecting fluid through axial pressure fluid supply line 42 and into fluid chamber 44, and the test sample fluid line 105 is monitored. The pressure is raised between 100-200 psi. The confining pressure is increased by injecting a fluid, such as mineral oil, through confining pressure fluid supply line 84 and into cell chamber 82 of the tri-axial test casing 26. Confining pressure can also be monitored using colored water so as to identify any leak occurring during the test. In instances where water is used, the water must first be degassed. Care should be taken to ensure that the axial stress remains above the confining stress. The test sample fluid line 105 can continue to be monitored to ensure that it remains in place. All the sample pressures, fluids, and temperature can then be equilibrated to desired test conditions.

The fluid sample holder 14 is then installed on the tri-axial test casing 26, the combination defining the tri-axial cell assembly 28. A data acquisition capsule, which can include one or more of processing units 66, 92, 114, and 144 can be added to the tri-axial cell assembly 28 and the tri-axial cell assembly 28, including the test sample 24, can be loaded in the centrifuge 16. Temperature, pressures, and fluids are equilibrated to desired test conditions. This second equilibrium step is related to usual movement (wobble) that is present in centrifuges at low RPM, and this must be monitored and equilibrated such that the fluid levels in the tri-axial cell assembly 28 are stable. The visual, x-ray, acoustic, and electrical data acquisition systems are started then the centrifuge test is started.

Embodiments of the present invention provide for data relating to saturation, capillary pressure, electrical properties, and permeability. Additionally, the range of temperatures, pressures, and fluids that can be used during the testing and analysis with this described apparatus is not available in the industry at this point. Embodiments of the present invention allow for testing of temperature, pressures, and fluids that mimic reservoir conditions. Thus, the testing parameters are dependent on reservoir condition and type of studies to be conducted.

The tri-axial stress test conditions, in combination with higher capillary pressure conditions, make it possible to test unconsolidated sand such as Alberta heavy oil tar sand, and perform various fluid injection regimes to extract heavy oil in a much shorter timeframe than done with conventional core flow setup based on flow rate. Also, the conventional core flow method is extremely dependent on the flow channel and therefore it is almost impossible to achieve any appreciable capillary pressure study permeability or saturation.

The tri-axial stress test conditions, along with higher capillary pressure conditions, x-ray saturation monitoring, fluid volume change in the fluid sample holder 14 as a function of time, and capillary pressure, provide for testing for shale (oil/gas). With conventional flow methods, the injection fluids cannot achieve the required high capillary pressure as the fluids find a channel to flow through and the rest of the test sample 24 does not experience the capillary pressure. In unstressed centrifugation, the sample has a much higher chance of failure. The added caveat in working with shale is its heterogeneity in matrix, layering and presence of kerogen. Due to these issues, historical analysis has relied on a crush test which delivers unreliable results for saturation, capillary pressure, and matrix permeability.

The tri-axial centrifuge apparatus 10 with its various data acquisition and high capillary pressure provides an avenue to perform fracture test analysis needed for hydraulic fracturing, especially in tight gas sand and shale. Given that shale is ductile, a tri-axial analysis provides the strength needed to keep the test sample intact. Tests on fractured cores with or without propant embedment provides differentiation of flow through the matrix versus fracture. This cannot be achieved with a conventional core flow test conducted in the industry, especially on un-conventional rock samples.

In further embodiments of the invention, a modified version of the apparatus will be operable at a well site with drill cuttings and mud/fluid analysis.

In further embodiments, integration of test data and measurements relating to sonic, resistivity (induction log), gamma and porosity (neutron logs) can be extended to wells where cores were not taken. Thus, extrapolation of data can allow for greater understanding of unsampled regions.

In yet further embodiments, the invention provides for fluid analysis under reservoir conditions to better understand phase behavior as a function of capillary pressure change, segregation of different density fluids, and separation of solids and their effects on sonic velocities. Additionally, fluid analysis related to formation damage and flow assurance can be performed. Analysis for formation damage is the same setup as described as for other analysis.

Since the components of the tri-axial centrifuge apparatus 10 are made of materials that are resistant to chemical damage, the various chemicals that cause formation damage can be used with the tri-axial centrifuge apparatus 10. For flow assurance, the effect of segregation of solids (asphaltene, wax, etc.) can be quantified during a phase behavior tests. The phase behavior test on reservoir fluids can also be conducted by filling the chamber with reservoir fluid under reservoir condition and centrifuging to separate various phases based on density using centrifugation gravitational forces. The acoustic sensor 20 and x-ray instrument 22 will assist in segregating various phases.

The tri-axial nature of the tri-axial centrifuge apparatus 10 provides the strength needed to increase the capillary pressure on the test sample 24 to much higher pressure than currently possible in existing centrifuges. The combination of the various data collected (x-ray, resistivity, acoustic, visual, etc.) provides a much needed comprehensive test instrument. The tri-axial centrifuge apparatus 10 also can increase data accuracy and efficiency of data delivery. The tri-axial centrifuge apparatus 10 also can provide cost savings as it allows for running tests simultaneously and provides more accurate reserve estimation, production profiles, and improves EOR planning In general, embodiments of the present invention improve the existing method of core and fluid testing, allow better control on data; improve test quality; reduce time for certain time critical data collection and analysis; provide a means of analyzing unconventional reservoirs such as, tight gas sand, shale (oil/gas), hydrate, tar sand, heavy oil, and low saturation reservoirs; provide a single source test apparatus to provide petrophysical data calibrated to electrical logs for saturation; provide a single source test apparatus for calibration of acoustic and seismic logs; provide a single source test apparatus for analysis of tri-axial stresses on petrophysical properties such as wettability, capillary pressure, permeability and saturation of various fluids; and provide a tri-axial centrifuge apparatus that works well both in a laboratory setting or in the field.

Although the present invention has been described in detail, it should be understood that various changes, substitutions, and alterations can be made hereupon without departing from the principle and scope of the invention. Accordingly, the scope of the present invention should be determined by the following claims and their appropriate legal equivalents.

The singular forms "a," "an" and "the" include plural references, unless the context clearly dictates otherwise.

Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

As used herein and in the appended claims, the words "comprise," "has," and "include" and all grammatical variations thereof are each intended to have an open, non-limiting meaning that does not exclude additional elements or steps.

What is claimed is:

1. A method of using a tri-axial centrifuge apparatus, said method comprising the steps of:
   providing the tri-axial centrifuge apparatus having:
   a tri-axial sample holder located within an inner bore of a cell body;
   an axially oriented piston assembly with a piston stem located entirely within the inner bore of the cell body, the axially oriented piston assembly operable to apply an axial pressure on a test sample that is greater than a biaxial confining fluid pressure applied on the test sample, and operable to apply the axial pressure independent of increasing the biaxial confining fluid pressure;
   a fluid sample holder, the fluid sample holder being sealingly secured to the cell body and static relative to the cell body;
   a test fluid circulation system having a test sample fluid line extending between the tri-axial sample holder and the fluid sample holder and a fluid circulation line extending outside of the cell body between the fluid sample holder and the tri-axial sample holder, the test fluid circulation system providing a fluid circulation path for a test fluid sample;

a centrifuge with a window that is located on a portion of a path of the tri-axial sample holder, where the test fluid circulation system rotates with the cell body within the centrifuge;

at least one electrical sensor;

at least one acoustic sensor; and an x-ray instrument, wherein the x-ray instrument is static and is aligned with the window of the centrifuge;

loading the test sample in the tri-axial sample holder;

loading the tri-axial sample holder within the inner bore of the cell body of a tri-axial test casing;

applying axial pressure to the test sample with the axially oriented piston assembly with the piston stem located entirely within the inner bore of the cell body;

increasing the biaxial confining fluid pressure in the tri-axial test casing, where the axial pressure is greater than the biaxial confining fluid pressure and applying the axial pressure is independent of increasing the biaxial confining fluid pressure;

equilibrating the pressure, fluid, and temperature for the test sample to a first test condition;

loading the fluid sample holder in the tri-axial test casing, the fluid sample holder being sealingly secured to the cell body and static relative to the cell body;

performing a centrifuge test on the test sample;

performing an x-ray scan of the test sample through the window of the centrifuge that is located on the path of the tri-axial sample holder with the x-ray instrument as the test sample spins past the x-ray instrument;

performing electrical analysis of the test sample; and performing acoustic analysis of the test sample.

2. A method of using the tri-axial centrifuge apparatus of claim 1, further comprising before performing the centrifuge test on the test sample, loading the test sample in the centrifuge in a vertical orientation that is parallel to an axis of rotation.

3. A method of using the tri-axial centrifuge apparatus of claim 1, further comprising before performing the centrifuge test on the test sample, loading the test sample in the centrifuge in a horizontal orientation that is perpendicular to an axis of rotation.

4. A method of using the tri-axial centrifuge apparatus of claim 1, wherein the performing electrical analysis of the test sample includes measuring at least one of the resistance, conductivity, capacitance, or impedance of the test sample.

5. A method of using the tri-axial centrifuge apparatus of claim 1, wherein the performing acoustic analysis of the test sample includes measuring sonic velocity data of the test sample.

6. A method of using the tri-axial centrifuge apparatus of claim 1, wherein the acoustic sensor rotates with the tri-axial test casing.

7. A method of using the tri-axial centrifuge apparatus of claim 1, wherein the biaxial confining fluid pressure is increased after the axial pressure is applied.

8. A method of using the tri-axial centrifuge apparatus of claim 1, further comprising providing open two way fluid communication between the tri-axial sample holder and the fluid sample holder.

9. A method of using the tri-axial centrifuge apparatus of claim 1, where performing the centrifuge test on the test sample includes providing a capillary pressure of at least 10,000 psi.

10. A method of using the tri-axial centrifuge apparatus of claim 1, where performing the centrifuge test on the test sample includes providing a capillary pressure of at least 20,000 psi.

11. A method of using the tri-axial centrifuge apparatus of claim 1, where the test fluid sample is a solvent.

12. A method of using the tri-axial centrifuge apparatus of claim 1, further including performing a saturation and a capillary pressure test at tri-axial test conditions.

* * * * *